(12) United States Patent
Mizuyoshi et al.

(10) Patent No.: US 8,876,706 B2
(45) Date of Patent: Nov. 4, 2014

(54) ENDOSCOPIC APPARATUS

(75) Inventors: Akira Mizuyoshi, Kanagawa (JP); Maki Saito, Kanagawa (JP); Takayuki Iida, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 155 days.

(21) Appl. No.: 13/591,378

(22) Filed: Aug. 22, 2012

(65) Prior Publication Data

US 2013/0053642 A1    Feb. 28, 2013

(30) Foreign Application Priority Data

Aug. 23, 2011    (JP) ................................. 2011-181593

(51) Int. Cl.
*A61B 1/06*    (2006.01)
*A61B 1/045*    (2006.01)
*A61B 1/00*    (2006.01)

(52) U.S. Cl.
CPC .............. *A61B 1/0684* (2013.01); *A61B 1/063* (2013.01); *A61B 1/0653* (2013.01); *A61B 1/0638* (2013.01); *A61B 1/045* (2013.01); *A61B 1/00006* (2013.01); *A61B 1/0669* (2013.01)
USPC ............................ 600/180; 600/178; 600/109

(58) Field of Classification Search
CPC .... A61B 1/0638; A61B 1/0653; A61B 1/063; A61B 1/0669; A61B 1/0019; H05B 33/0869
USPC ........................ 600/109, 178, 180, 181–182
See application file for complete search history.

(56) References Cited

U.S. PATENT DOCUMENTS

| | | |
|---|---|---|
| 2009/0062617 A1* | 3/2009 | Mizuyoshi ................. 600/178 |
| 2009/0221875 A1 | 9/2009 | Kobayashi |
| 2011/0032350 A1 | 2/2011 | Kikuchi et al. |
| 2011/0034770 A1 | 2/2011 | Endo et al. |
| 2011/0069163 A1 | 3/2011 | Ozawa et al. |
| 2011/0071353 A1 | 3/2011 | Ozawa et al. |

FOREIGN PATENT DOCUMENTS

| | | |
|---|---|---|
| EP | 2452611 A1 | 5/2012 |
| JP | 2009-201940 A | 9/2009 |

* cited by examiner

*Primary Examiner* — John P Leubecker
*Assistant Examiner* — Arnaldo Torres Diaz
(74) *Attorney, Agent, or Firm* — Birch, Stewart, Kolasch & Birch, LLP

(57) ABSTRACT

According to an aspect of the invention, an endoscopic apparatus outputs illuminating light from a tip of an endoscope inserting module to a subject and detects a reflected light from the subject to obtain an image signal of the subject. The endoscopic apparatus includes a first light source, a second light source, a target light intensity setting module, a light intensity ratio setting module, an information storing module, an amplitude value setting module, a driving signal generating module, a signal supplying module.

18 Claims, 5 Drawing Sheets

ENDOSCOPIC APPARATUS

CROSS-REFERENCE TO RELATED APPLICATIONS

This application claims the benefit of Japanese Patent Application No. 2011-181593 (filed on Aug. 23, 2011), the entire contents of which are hereby incorporated by reference.

BACKGROUND

1. Technical Field

The present invention relates to an endoscopic apparatus.

2. Related Art

An endoscopic device that observes tissues in the body cavity is widely known. Generally, the endoscopic device is configured to irradiate white light (irradiation light) emitted from a white light source such as a xenon lamp onto a subject area to be observed in the body cavity through a light guide and receive the image based on the reflected light from the subject area to be observed by an image pickup device to create an observation image.

Recently, an endoscopic device having observation modes using special light such as narrow band observation that irradiates narrow band light having a specific wavelength band onto a body tissue to observe the blood capillary or a micro pattern of a superficial portion of the mucous membrane or fluorescent observation by auto fluorescence or medicine fluorescence is also used. As the special light, a mixture of light from a white light source such as a xenon lamp and narrow band light from a semiconductor light source such as a laser diode is known (JP-A-2009-201940).

According to the method disclosed in JP-A-2009-201940, since the xenon lamp is used as the white light source, it is difficult to minutely control an emitted light intensity ratio of the white light and the narrow band light. Therefore, instead of the xenon lamp as the white light source, a light source configured by combining a light emitting diode (LED) having long life span and low output variation and a fluorescent may be used. As described above, when two semiconductor light sources are used as the light sources for the special light observation, the output of the semiconductor light sources can be minutely controlled, so that the wavelength balance (emitted light intensity ratio) may be precisely set.

However, it is not easy to modulate the intensity of the light sources while maintaining the wavelength balance of the two semiconductor light sources at a high precision. Specifically, when using a light source, such as an LED, that has a region in which the characteristic of the emitted light intensity with respect to an input current value is nonlinear, it is required to control in consideration of the nonlinearity.

SUMMARY OF INVENTION

The present invention has been made in an effort to, when the special light observation is performed by an endoscopic device that uses two light sources at least including a semiconductor light source having a region in which the characteristic of the emitted light intensity with respect to an input current value is nonlinear, maintain the mixing ratio of light in two light sources at a high precision and obtain a desired observation image.

According to an aspect of the invention, an endoscopic apparatus outputs illuminating light from a tip of an endoscope inserting module to a subject and detects a reflected light from the subject to obtain an image signal of the subject.

The endoscopic apparatus includes a first light source, a second light source, a target light intensity setting module, a light intensity ratio setting module, an information storing module, an amplitude value setting module, a driving signal generating module, a signal supplying module.

The first light source includes a first semiconductor light source having a relation between a light intensity of the first semiconductor light source and an amplitude value of a driving signal inputted to the first semiconductor light source, a part of the first relation being nonlinear.

The second light source includes a second semiconductor light source emitting second light having different main wavelength component from the first light source.

The target light intensity setting module sets a target light intensity for a sum of emitted light intensities from the first light source and the second light source.

The light intensity ratio setting module sets an emitted light intensity ratio between the first light source and the second light source.

The information storing module stores information representing relations between an amplitude value of imputed driving signal and the emitted light intensity for each of the first light source and the second light source;

The amplitude value setting module sets a first amplitude value of the driving signal to be supplied to the first light source and a second amplitude value of the driving signal to be supplied to the second light source based on the emitted light intensity ratio set by the light intensity ratio setting module, the information stored in the information storing module, and the target light intensity set by the target light intensity setting module.

The driving signal generating module generates a common driving signal common to the first light source and the second light source based on the target light intensity, generates a first driving signal for the first light source by changing the amplitude value of the common driving signal into the first amplitude value, and generates a second driving signal for the second light source by changing the amplitude value of the common driving signal into the second amplitude value.

The signal supplying module controls the sum of the emitted light intensities to be the target light intensity by supplying the first driving signal to the first light source and supplying the second driving signal to the second light source, respectively.

According to the present invention, when the special light observation is performed by an endoscopic device that uses two light sources at least including a semiconductor light source having a region in which the characteristic of the emitted light intensity with respect to an input current value is nonlinear, it is possible to obtain a desired observation image by maintaining the mixing ratio of light in two light sources at a high precision.

DETAILED DESCRIPTION

Hereinafter, exemplary embodiments of the present invention will be described with reference to the accompanying drawings.

Figure 1:
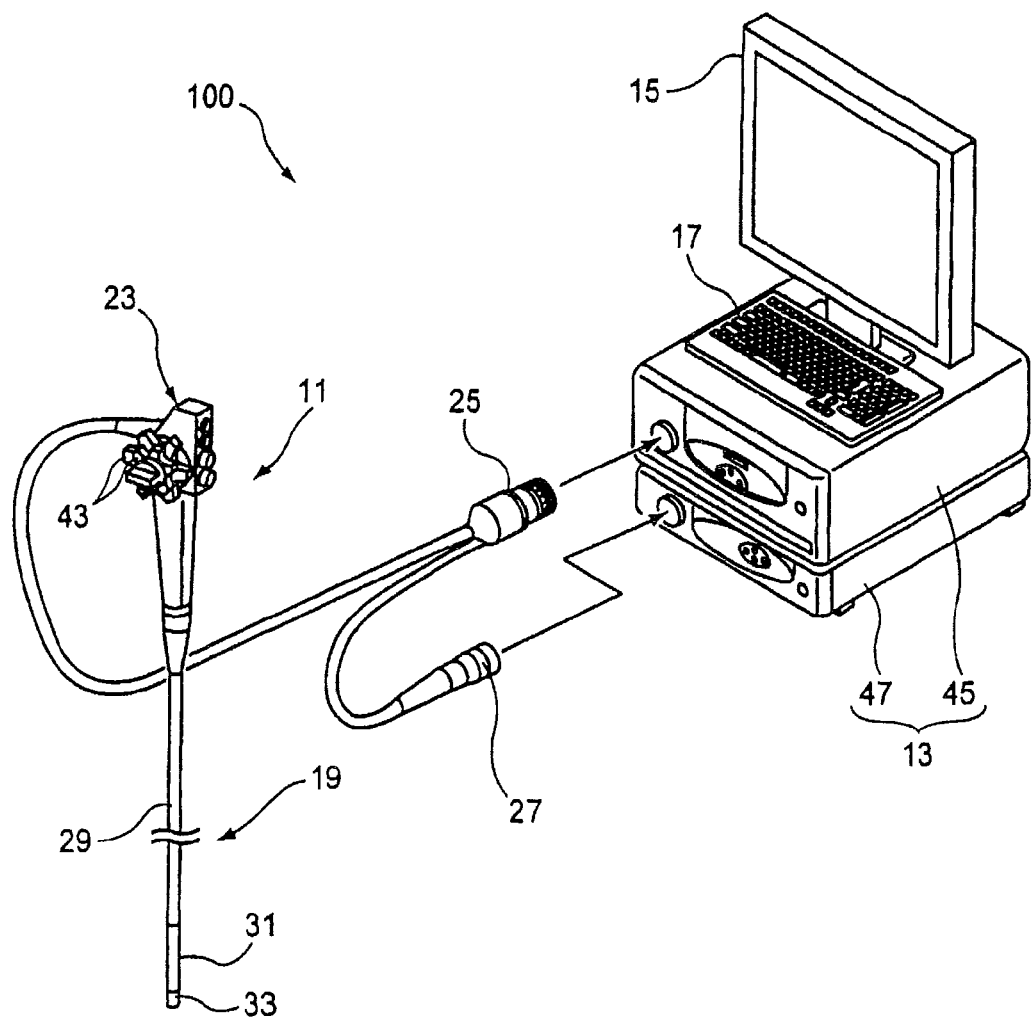
FIG. 1 is an external view of an endoscopic device 100 according to an exemplary embodiment of the present invention.

FIG. 1 is an external view of an endoscopic device 100 according to an exemplary embodiment of the present invention.

The endoscopic device 100 includes an endoscope 11, a control device 13, a display module 15 such as a liquid crystal display, and an input module 17 such as a keyboard or a mouse that inputs information to the control device 13.

The control device 13 includes a light source device 45 and a processor 47 that performs signal processing of a captured image signal output from the endoscope 11.

The endoscope 11 includes an endoscope inserting module 11 that is inserted into a subject, a manipulating module 23 that is manipulated for observation or bending operation of a front edge of the endoscope inserting module 19, and connector modules 25, 27 that connect the endoscope 11 to the control device 13 so as to be detachable.

The endoscope inserting module 19 is configured by a flexible part 29 having flexibility, a curvature part 31, and a front edge part (hereinafter, referred to as an endoscope front edge part) 33.

Even though not shown in the drawing, in the inside of the manipulating module 23 and the endoscope inserting module 19, various kinds of channels such as a clamp channel to which a treatment tool for tissue collection or a channel for supplying air or water are provided.

Figure 2:
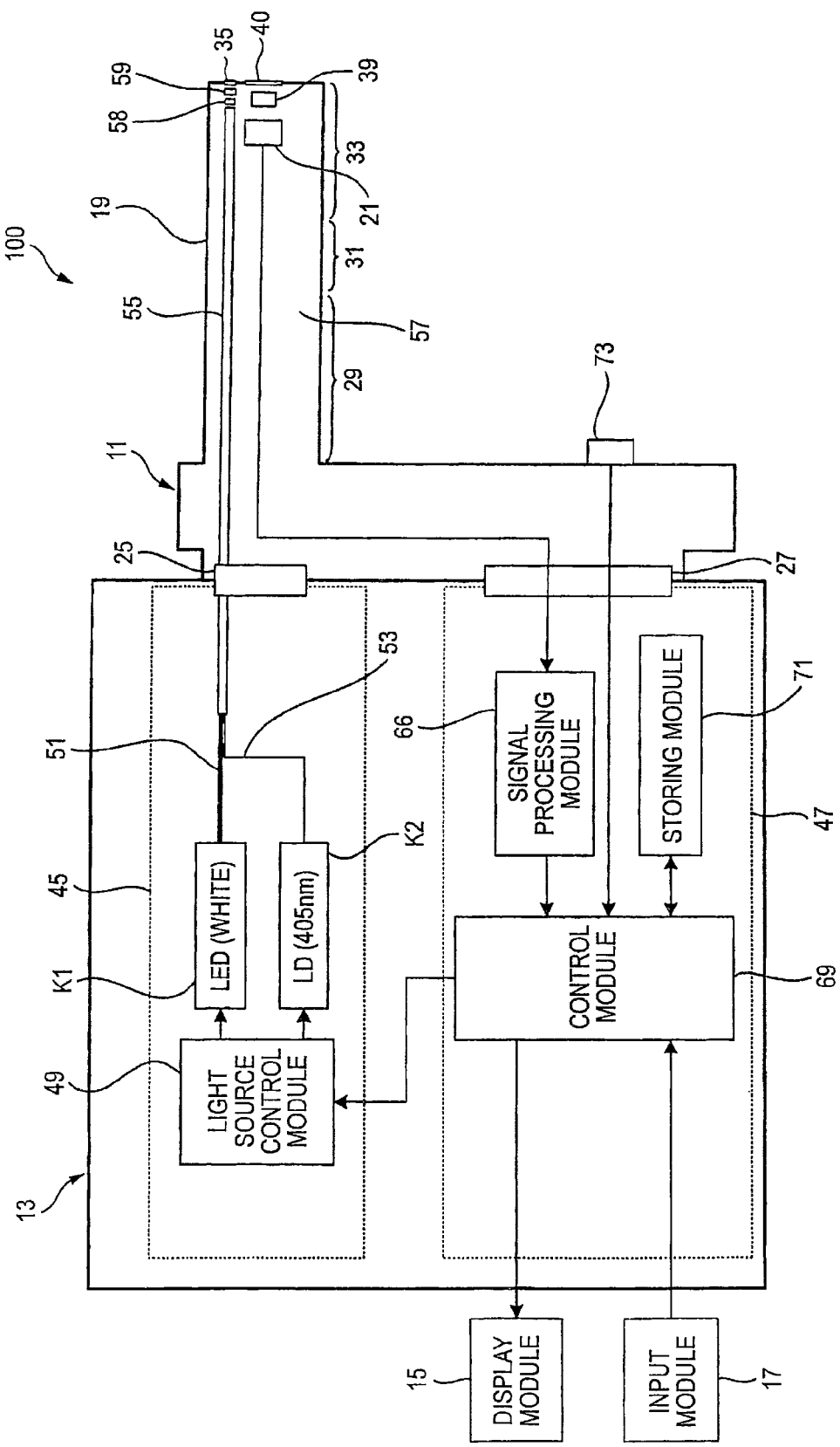
FIG. 2 is a view illustrating an internal configuration of the endoscopic device 100 shown in FIG. 1.

FIG. 2 is a view illustrating an internal configuration of the endoscopic device 100 shown in FIG. 1.

The endoscope front edge part 33 includes an illumination window 35 that irradiates light onto a subject region to be observed, a diffuser 58 disposed so as to oppose to the illumination window 35, an illuminating lens 59 disposed between the diffuser 58 and the illumination window 35, an image pickup device 21 such as a charge coupled device (CCD) type image sensor or a complementary metal-oxide semiconductor (CMOS) image sensor that receives the reflection light from the subject region to be observed, an observation window 40 that allows the reflection light in the subject region to be observed to be incident onto a light receiving surface of the image pickup device 21, and an objective lens unit 39 that is provided between the observation window 40 and the image pickup device 21.

The curvature part 31 is provided between the flexible part 29 and the front edge part 33 so as to be curved by turning an angle knob 43 (see FIG. 1) disposed in the manipulating module 23.

The curvature part 31 may be curved in an arbitrary direction and at an arbitrary angle in accordance with a portion of the subject to which the endoscope 11 is used and allow the illumination window 35 and the observation window 40 of the endoscope front edge part 33 to be oriented to a desired observation portion.

The control device 13 includes a light source device 45 that generates the illuminating light that is supplied from the illumination window 35 of the endoscope front edge part 33 to the subject region to be observed, and a processor 47 that processes R, G, and B captured image signals output from the image pickup device 21. The light source device 45 and the processor 47 are connected to the endoscope 11 through connector modules 25, 27, respectively.

The light source device 45 includes a light source control module 49, a light source K1 that emits white light using an LED as a light emitting source, a light source K2 that emits a narrow band light having a central wavelength of 405 nm, and an optical fiber bundle 51, and an optical fiber 53.

Figure 4:
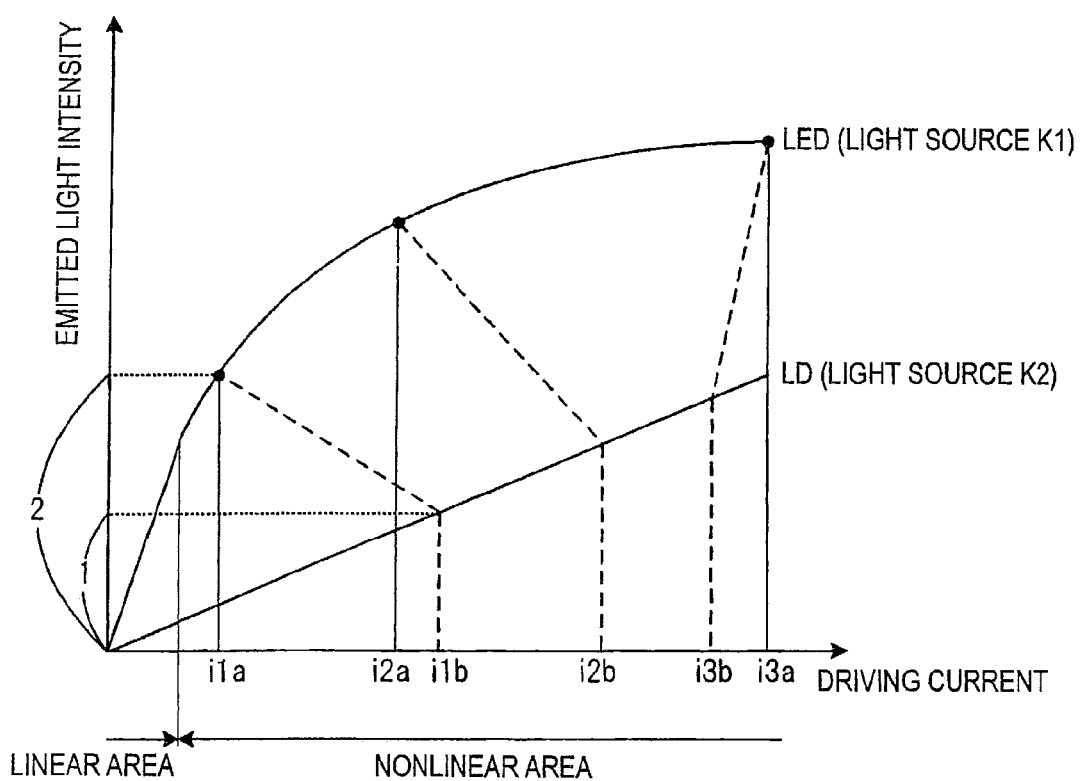
FIG. 4 is a view illustrating the relationship between an amplitude value of a driving pulse that is supplied to the light sources K1, K2 and an emitted light intensity of the light sources K1, K2.

The light source K1 is a light source for normal observation (white light observation). The light source K1 is configured by an LED and a fluorescent substance that covers the LED. In the present embodiment, the light source K1 is configured by an LED that emits blue light having a wavelength of 445 nm and a YAG-based fluorescent substance that emits yellow fluorescence using the light emitted from the LED as excited light. The yellow light that is excited by some of the blue light emitted from the LED and the blue light that transmits the fluorescence substance are added so as to emit the white light from the light source K1. The light source K1 includes the LED, so that, as shown in FIG. 4, which will be described below, the light source K1 has a region in which the characteristic of the emitted light intensity with respect to the amplitude value (input current value) of the driving signal is nonlinear.

The light source K2 is a light source for narrow band observation and is configured by a semiconductor element. As the light source K2, a laser diode of which the emitted light intensity has a linear characteristic with respect to the amplitude value of the driving signal or an LED having a region in which the emitted light intensity with respect to the amplitude value of the driving signal is nonlinear may be employed. A specific example thereof may include a semiconductor laser that emits violet light having a central wavelength of 405 nm. As the laser light source, broad area type InGaN-based laser diode may be used. If a central wavelength of the emitted light of the light source K2 is in the range between 370 nm and 470 nm, good narrow band observation in which the blood capillary or a micro pattern of a superficial portion of the mucous membrane is emphasized is allowed.

The light emitted from the light sources K1, K2 is individually controlled by the light source control module 49. The light source control module 49 has only the light source K1 emit light at the normal observation mode. The light source control module 49 has only the light source K2 emit light at the fluorescent observation mode. Further, the light source control module 49 has the light source K1 and K2 concurrently emits light at a predetermined light intensity ratio in the narrow band observation mode that is for observing the blood capillary or the micro pattern of a superficial portion of the mucous membrane.

Figure 3:
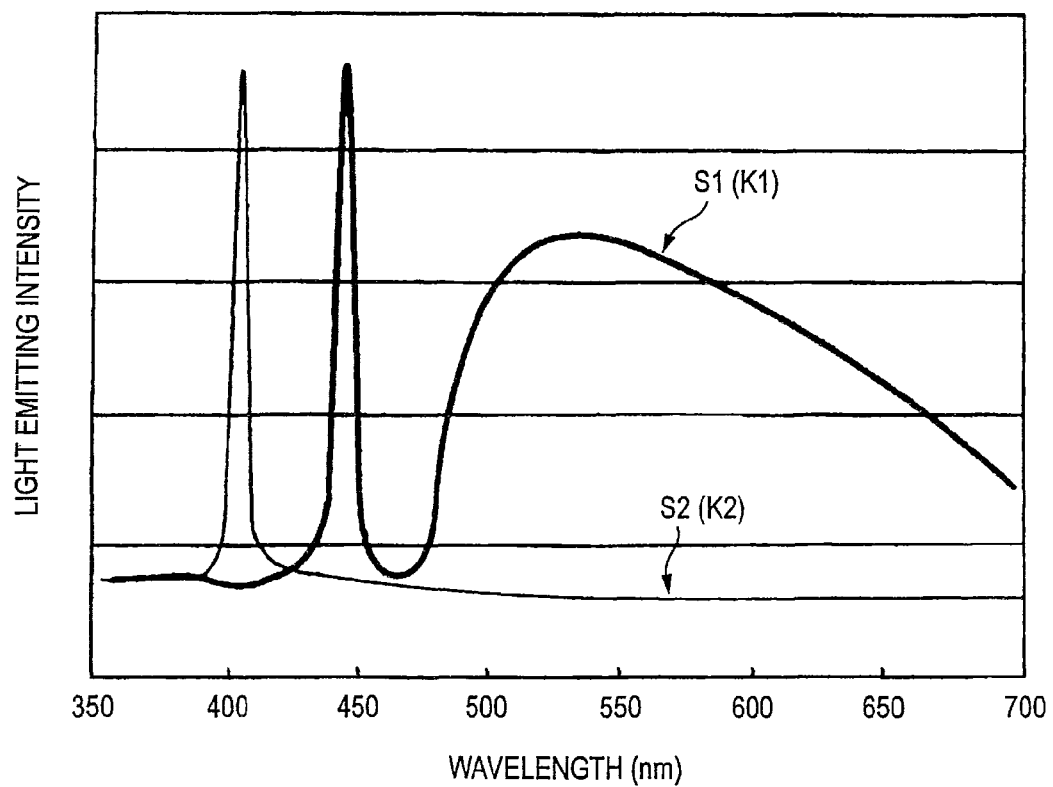
FIG. 3 is a view illustrating the relationship between the wavelength and the emitted light intensity of light emitted from light sources K1, K2.

FIG. 3 is a view illustrating the relationship between the wavelength and the emitted light intensity of light emitted from light sources K1, K2.

In FIG. 3, S1 denotes the light emitted from the light source K1 and S2 denotes the light emitted from the light source K2. As shown in FIG. 3, the intensity of the light emitted from the light source K2 in the range of the wavelength of 445 nm or more is low. Therefore, the emitted light intensity ratio between the light sources K1 and K2 is precisely controlled. The change in the light intensity in the light source K2 does not substantially affect the white light of the light source K1. As a result, it is possible to make the image quality at the narrow band observation better.

The white light emitted from the light source K1 is input to the optical fiber bundle 51 by a condensing lens (not shown). The violet light emitted from the light source K2 is input to the optical fiber 53 by a condensing lens (not shown). The optical fiber bundle 51 and the optical fiber 53 are tied together by a light guide 55. The light guide 55 extends to the endoscope front edge part 33 through the connector 25. The light emitted from the sectional surface at the endoscope front edge part 33 side of the light guide 55 is diffused to the diffuser 58 and is emitted from the observation window 35 through the lens 59.

The light source control module 49 controls the light sources K1, K2 by pulse driving. That is, the light source control module 49 supplies the driving signal (pattern of the driving pulse) to the light sources K1, K2. During the period when the driving pulse is at a high level, the light sources K1, K2 emit the light.

The above-mentioned display module 15 and the input module 17 are connected to the processor 47. The processor 47 includes the signal processing module 66, the control module 69, and the storing module 71.

The signal processing module 66 processes the captured image signal transmitted from the endoscope 11 in response to the command from the manipulating module 23 or the input module 17 of the endoscope 11 to generate captured image data. The signal processing module 66 calculates brightness information (brightness information of the subject image) of the captured image signal from the captured image signal transmitted from the endoscope 11 and outputs the brightness information to the control module 69. The captured image data generated in the signal processing module 66 is reproduced in the display module 15 or is stored in the storing module 71 by the control of the control module 69.

In the storing module 71, a brightness-target light intensity table is stored, in which the brightness information of the captured image signal and a value of the target light intensity for one frame of the light emitted from the light source device 45 are associated with each other.

In the storing module 71, a table for the light source K1 in which an amplitude value (driving current value) of the driving pulse configuring the driving signal supplied to the LED of the light source K1 is associated with the emitted light intensity (light intensity emitted with one driving pulse) of the light source K1 per unit time and a table for the light source K2 in which an amplitude value (driving current value) of the driving pulse configuring the driving signal supplied to the light source K2 is associated with the emitted light intensity (light intensity emitted with one driving pulse) of the light source K2 per unit time, are stored. As shown in FIG. 4, the relationship between the driving current of the light source K1 and the emitted light intensity is linear to a predetermined driving current, but is nonlinear over the predetermined driving current. The relationship between the driving current of the light source K2 and the emitted light intensity is linear over the entire area.

The control module 69 calculates a target light intensity corresponding to the brightness information by the brightness information input from the signal processing module 66 and the brightness-target intensity table stored in the storing module 71 to transmit the information of the target light intensity to the light source control module 49.

Based on the information of the target light intensity received from the control module 69, the emitted light intensity ratio per one driving pulse of the light sources K1, K2 set by the control module 69 and the tables for the light sources K1, K2 stored in the storing module 71, the light source control module 49 generates the driving signal where all of the emitted light intensity that is obtained by adding the individual emitted light intensities in one frame of the light sources K1, K2 becomes the target light intensity while maintaining the emitted light intensity ratio per one driving pulse of the light sources K1, K2 at a set value, and then supplies the driving signal to the light sources K1, K2 during the narrow band observation period.

Hereinafter, the operation of the endoscopic device 100 in the narrow band observation mode will be described.

First, the operator presses an observation mode switching button 73 (see FIG. 2) that functions as an observation mode selecting module provided in the endoscope 11 so that the control module 69 performs control to switch various observation modes such as the normal observation, the narrow band observation or the fluorescent observation. The control module 69 sets the emitted light intensity ratio Ra:Rb of the light sources K1, K2 to 1:0 in the normal observation mode. The control module 69 sets the emitted light intensity ratio Ra:Rb to be a predetermined ratio, for example, 2:1, in the narrow band observation mode. The control module 69 sets the emitted light intensity ratio Ra:Rb to 0:1 in the fluorescent observation mode.

In the narrow band observation mode, while the light source control module 49 maintains the outputs of both light sources K1, K2 at the above-mentioned emitted light intensity ratio, the light source control module 49 controls all of the emitted light intensity from the light sources K1, K2 to be a target light intensity. Hereinafter, the procedures of generating desired illuminating light by driving the light sources K1, K2 in the narrow band observation mode will be described.

First, the control module 69 reads out the emitted light intensity ratio Ra:Rb (hereinafter, it is considered that Ra=2 and Rb=1) of the light sources K1, K2 corresponding to the narrow band observation mode from the storing module 71, and then transmits the emitted light intensity ratio to the light source control module 49. The light source control module 49 receives the information of the emitted light intensity ratio Ra:Rb, and sets the emitted light intensity ratio Ra:Rb as a designated emitted light intensity ratio.

When the captured image signal is input to the signal processing module 66, the signal processing module 66 generates brightness information from the captured image signal. The control module 69 sets the target light intensity based on the brightness information and the brightness-target light intensity table stored in the storing module 71, and then transmits the information of the target light intensity to the light source control module 49.

Next, the light source control module 49 sets an amplitude value (driving current value) of the driving pulse that configures the driving signal that is supplied to the light sources K1, K2 based on the information of the emitted light intensity ratio of 2:1 received from the control module 69, the tables for the light sources K1, K2 stored in the storing module 71, and the information of the target light intensity received from the control module 69.

Specifically, if the target light intensity is higher than a threshold, the light source control module 49 sets the amplitude values of the driving pulses supplied to the light sources K1, K2 to a predetermined reference value (for example, the combination of the amplitude values when the amplitude value of the light source K1 becomes a maximum). If the target light intensity is lower than the threshold, the light source control module 49 sets the amplitude values of the driving pulses supplied to the light sources K1, K2 to a value corresponding to the target light intensity.

For example, as shown in FIG. 4, if the target light intensity is higher than the threshold, the light source control module 49 sets the amplitude value of the driving pulse supplied to the light source K1 as the amplitude value $i3a$ of the maximum value, and the amplitude value $i3b$ when a light intensity is half the emitted light intensity at the amplitude value $i3a$ is set as the amplitude value of the driving pulse that is supplied to the light source K2. In contrast, if the target light intensity is lower than the threshold, the light source control module 49 set the amplitude values of the driving pulses that are supplied to the light sources K1, K2 to be smaller, as the target light intensity becomes lower.

Regardless of the value of the target light intensity, the light source control module 49 sets the amplitude values of the driving pulses that are supplied to the light sources K1, K2 so that (emitted light intensity of the light source K1 per unit time):(emitted light intensity of the light source K2 per unit time) is always 2:1.

For example, if the target light intensity is a predetermined value that is lower than the threshold, the light source control module 49, as shown in FIG. 4, sets the amplitude value of the driving pulse supplied to the light source K1 as the amplitude value i2a and the amplitude value i2b when the light intensity is half the emitted light intensity at the amplitude value i2a is set as the amplitude value of the driving pulse that is supplied to the light source K2. If the target light intensity is smaller than the predetermined value, the light source control module 49 sets the amplitude value of the driving pulse that is supplied to the light source K1 as the amplitude value i1a, and the amplitude value i1b when the light intensity is half of the emitted light intensity at the amplitude value i1a is set to the amplitude value of the driving pulse that is supplied to the light source K2.

Next, if the target light intensity is higher than the threshold, the light source control module 49 generates a common driving signal (pattern of the driving pulse) of the light sources K1, K2 in accordance with the target light intensity. The light source control module 49 generates a value obtained by changing the amplitude value of the driving pulse that configures the common driving signal of the light sources K1, K2 into a value set for the light source K1 as a driving signal for the light source K1. Further, the light source control module 49 generates a value obtained by changing the amplitude value of the driving pulse that configures the common driving signal of the light sources K1, K2 into a value set for the light source K2 as a driving signal for the light source K2.

The light source control module 49 generates diving signals for the light sources K1, K2 in which all of the emitted light intensity becomes the target light intensity by performing pulse number modulation (PNM) that changes the driving pulse number included in the driving signal in a range from a first value of the target light intensity to a second value that is lower than the first value. The first value is an upper limit (a value when the amplitude value of the driving pulse supplied to the light sources K1, K2 is a reference value) in a design that can be emitted from the light source device.

The light source control module 49 generates driving signals for the light sources K1, K2 in which all of the emitted light intensity becomes the target light intensity by performing pulse density modulation (PDM) that changes the density of the driving pulse on the driving signal whose driving pulse number is reduced to a limit by the pulse number modulation (PNM) in a range from the second value of the target light intensity to the threshold which is lower than the second value.

Figure 5:
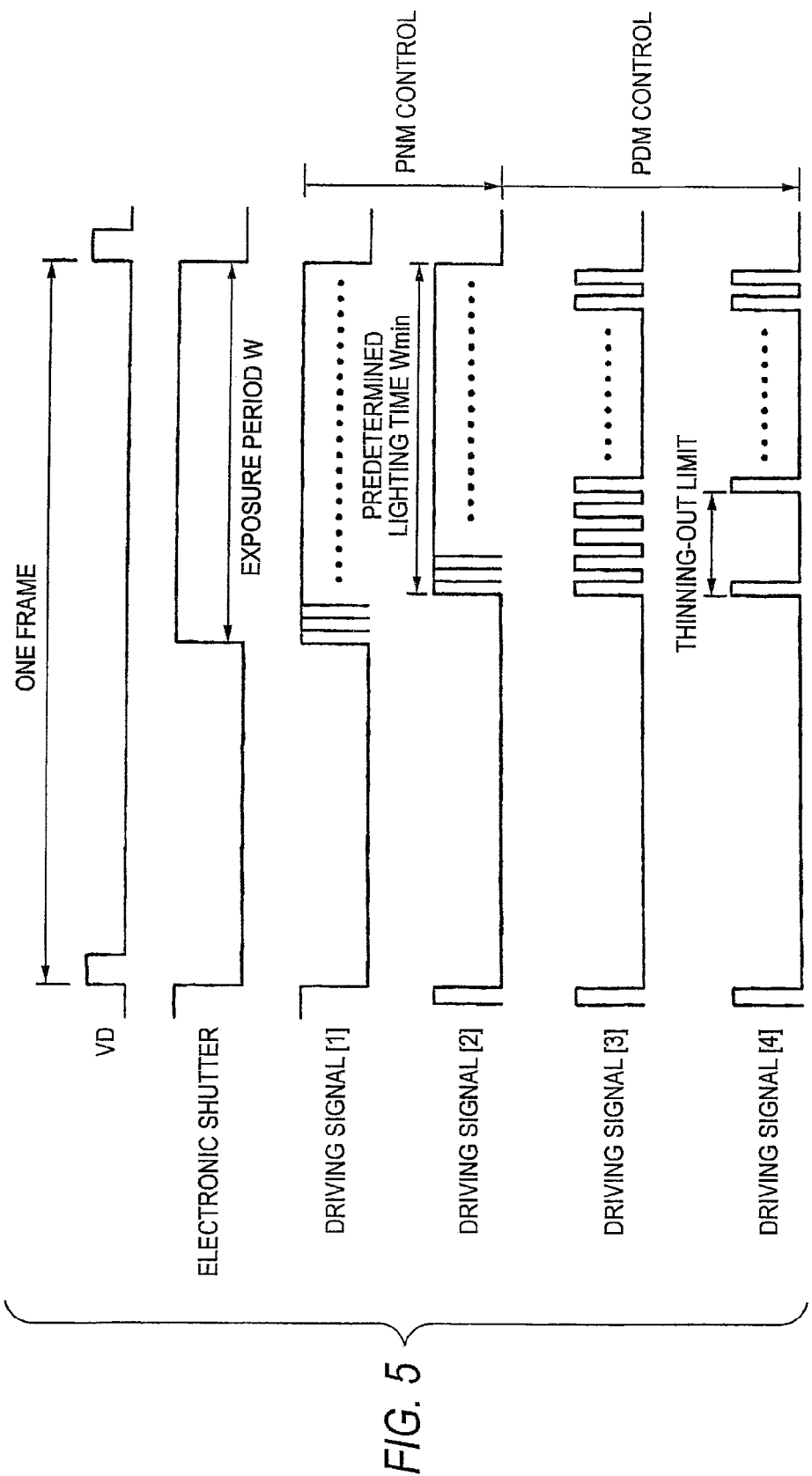
FIG. 5 is a view illustrating an example of a driving signal common to the light sources K1, K2 that is generated by a light source control module 49.

FIG. 5 is a view illustrating an example of a driving signal common to the light sources K1, K2 that is generated by the light source control module 49

When the target light intensity is a design upper limit of all of the emitted light intensity that can be emitted from the light source device 45, the light source control module 49 generates a driving signal [1] that is configured by a pattern of a driving pulse that turns ON the light source over the exposure period W controlled by an electronic shutter, within one frame period of an image defined by a vertical synchronization signal VD.

When the target light intensity is reduced from the design upper limit, the light source control module 49 generates a driving signal that reduces the driving pulse number by backward pulse stuffing for a time axis with respect to the driving signal [1]. A driving signal [2] shown in FIG. 5 is represented as a signal when the driving pulse number is reduced so as to delay the starting timing of supplying the driving pulse until the driving pulse number of the driving signal [2] becomes a predetermined minimum ratio with respect to the driving signal [1]. The light source control module 49 increases the reduced number of the driving pulse with respect to the driving signal [1] as the target light intensity becomes lower.

After the lighting time of the light source that is determined by the reduction of the number of driving pulses reaches the PNM control limitation ("Wmin" of FIG. 5), when the target light intensity is further reduced, the light source control module 49 generates a driving signal [3] which is generated by thinning out a given number of the driving pulse of the driving signal [2]. The light source control module 49 increases the thinning-out rate of the driving pulse of the driving signal [2] as the target light intensity becomes lower.

A driving pulse [4] of FIG. 5 is a pulse when an interval of the driving pulses in the driving signal commonly generated for the light sources K1, K2 reaches the PDM control limit. When the target light intensity is equal to the threshold, the light source control module 49 generates a driving signal that is generated by changing the amplitude value of the driving pulses of the driving signal [4] into a reference value of the amplitude value set for the light sources K1, K2. In other words, all of the emitted light intensity emitted from the light source device 45 in accordance with the driving signal is set as the threshold of the above-mentioned target light intensity.

When the target light intensity is lower than the threshold, since the pulse modulation control has already reached the limit, it is difficult to obtain the target light intensity by the pulse modulation control. Therefore, in this case, the light source control module 49 sets the amplitude values (reference values) of the driving pulses set for the light sources K1, K2 to values that are reduced in accordance with the target light intensity.

For example, in a case where the amplitude values (reference values) of the driving pulses set for the light sources K1, K2 when the target light intensity are higher than the threshold are i3a and i3b, as shown in FIG. 4, the light source control module 49 calculates the amplitude values (for example, i2a and i2b) of the driving pulses that are supplied to the light sources K1, K2 so that all of the emitted light intensity becomes the target light intensity while maintaining the emitted light intensity ratio at predetermined values based on the tables for the light sources K1, K2 stored in the storing module 71, the information of the target light intensity, and the emitted light intensity ratio determined depending on the observation mode, and then sets the amplitude values as an amplitude values of the driving pulses that are supplied to the light sources K1, K2.

The number of driving pulses included in the driving signal [4] is known and the emitted light intensity ratio of the light sources K1, K2 with respect to the amplitude values of the driving pulses is known by the tables for the light sources K1, K2. Therefore, the light source control module 49 may calculate the amplitude values that can be reduced to obtain the target light intensity based on the above information.

The light source control module 49 generates a driving signal for the light source K1 in which the amplitude value of the driving pulse of the driving signal [4] shown in FIG. 5 is i2a, and a driving signal for the light source K2 in which the amplitude value of the driving pulse of the driving signal [4] shown in FIG. 5 is i2b. The light source control module 49 supplies the two driving signals to the light sources K1, K2, respectively. Accordingly, even though the target light intensity is below the threshold, all of the emitted light intensity is controlled to be the target light intensity while maintaining the emitted light intensity ratio of 2:1.

As described above, the light source control module 49 generates a driving signal corresponding to the target light intensity commonly to the light sources K1, K2, and then generates the driving signals for the light sources K1, K2 by changing the amplitude values of the common driving signal, respectively. When the target light intensity is changed between the upper set limit of all of the emitted light intensity that can be emitted from the light source device 45 and the threshold, the wave patterns of the driving signals are commonly changed while the amplitude values of the driving signals are fixed. Accordingly, the emitted light intensity ratio is fixed and the light intensity ratio of the light emitted from the light sources K1, K2 is not varied even though the pulse modulation control is performed in accordance with the change in the target light intensity. When the target light intensity is below the threshold, the amplitude value of the driving signals is changed in accordance with the target light intensity while the wave patterns of the driving signals are fixed and the emitted light intensity ratio is maintained. By doing this, even though the target light intensity is reduced to the limit of the pulse modulation control, it is possible to match all of the emitted light intensity to the target light intensity and constantly maintains the light intensity ratio of the light emitted from the light sources K1, K2.

The endoscopic device 100 sets the amplitude values of the driving pulses that are supplied by the light source control module 49 to the light sources K1, K2 using the tables for the light sources K1, K2 stored in the storing module 71. Therefore, only with the configuration of the exemplary embodiment that adopts the LED having a region where the characteristic of the emitted light intensity is non-linear, the emitted light intensity ratio of the light sources K1, K2 may be precisely controlled.

In the endoscopic device 100, the driving signal according to the target light intensity is commonly used for the light sources K1, K2. For this reason, as compared with the driving signals for the light sources K1, K2 that are individually pulse modulation controlled, the modulation control may be simple. Only comprising the plurality of light sources, the pulse modulation control for the target light intensity ratio of the light sources may be communalized by all of the light sources and the complex driving circuit may be avoided.

In the endoscopic device 100, when the target light intensity is higher than the threshold, the amplitude value of the light source K1 is set to the maximum value that can be set. The change in the color shade of the LED used for the light source K1 is increased as the amplitude value (driving current value) becomes larger. When the target light intensity is higher than the threshold, the capturing circumstance is bright so that the change in the color shade is easily noticeable. Therefore, when the target light intensity is larger than the threshold, if the amplitude value of the light source K1 is set to the maximum that can be set, it is preferable to prevent the deterioration of the image quality caused by the change in the color shade. In the endoscopic device 100, when the target light intensity is lower than the threshold, the amplitude value of the light source K1 is reduced to be lower than the maximum. However, in this case, the subject is dark and the change in the color shade is hard to notice, and therefore, the influence on the image quality is limited.

In the endoscopic device 100, the light source K1 may be provided in the endoscope front edge part 33 rather than the light source device 45. In this case, the light source K1 may be exchanged into another kind by, for example, an adaptor. When the light source K1 is exchanged into another kind, only by rewriting the table for the light source K1 stored in the storing module 71 with new data, the light source control module 49 may perform the above-mentioned control.

In the above description, the light source K1 emits white light and the light source K2 emits narrow band light. However, if the light sources K1, K2 emit light having different wavelength bands, the wavelength band of the emitted light is not limited to the combination of the white light and the narrow band light.

In the above description, the light emitting property of the light source K1 has a nonlinear region (LED+fluorescent substance) and the light emitting property of the light source K2 is linear (LD). However, the present invention is not limited thereto. Each of the light sources K1, K2 may have nonlinear region as the light emitting property (for example, combination of a light source configured by a LED+fluorescent substance and a light source configured by a LED).

As described above, the present specification discloses the following aspects.

(1) An endoscopic apparatus that outputs illuminating light from a tip of an endoscope inserting module to a subject and detects a reflected light from the subject to obtain an image signal of the subject, the endoscopic apparatus comprising:

a first light source that includes a first semiconductor light source having a relation between a light intensity of the first semiconductor light source and an amplitude value of a driving signal inputted to the first semiconductor light source, a part of the first relation being nonlinear;

a second light source that includes a second semiconductor light source emitting second light having different main wavelength component from the first light source;

a target light intensity setting module that sets a target light intensity for a sum of emitted light intensities from the first light source and the second light source;

a light intensity ratio setting module that sets an emitted light intensity ratio between the first light source and the second light source;

an information storing module that stores information representing relations between an amplitude value of imputed driving signal and the emitted light intensity for each of the first light source and the second light source;

an amplitude value setting module that sets a first amplitude value of the driving signal to be supplied to the first light source and a second amplitude value of the driving signal to be supplied to the second light source based on the emitted light intensity ratio set by the light intensity ratio setting module, the information stored in the information storing module, and the target light intensity set by the target light intensity setting module;

a driving signal generating module that generates a common driving signal common to the first light source and the second light source based on the target light intensity, generates a first driving signal for the first light source by changing the amplitude value of the common driving signal into the first amplitude value, and generates a second driving signal for the second light source by changing the amplitude value of the common driving signal into the second amplitude value; and a signal supplying module that controls the sum of the emitted light intensities to be the target light intensity by supplying the first driving signal to the first light source and supplying the second driving signal to the second light source, respectively.

(2) The endoscopic apparatus according to the aspect (1) further comprising:

an image capturing module that captures the subject by adjusting an exposure period by an electronic shutter, wherein the driving signal generating module generates the common driving signal by performing, in the descending order of the target light intensity, when the target light intensity is in a range between a maximum intensity of the sum of the emitted light intensities and a threshold, a first pulse modulation control that reduces the number of driving pulses included in the driving signal until a predetermined lighting period for an exposure period in the one frame of the electronic shutter and a second pulse modulation control that reduces a density of the driving pulse by thinning-out the driving pulse, the driving signal generating module generates the driving signal where the density of the driving pulse is reduced to the limitation by the second pulse modulation control as the common driving signal when the target light intensity is lower than the threshold, the amplitude value setting module sets a predetermined amplitude value in the information as the first amplitude value and sets an amplitude value as the second amplitude value so that a ratio between the emitted light intensity from the first light source by the first amplitude value and the emitted light intensity from the second light source by the amplitude value becomes the light intensity ratio set by the light intensity setting module when the target light intensity is in the range from the maximum intensity to the threshold, and the amplitude value setting module sets the first amplitude value and the second amplitude value depending on the target light intensity when the target light intensity is lower than the threshold.

(3) The endoscopic apparatus according to the aspect (2), wherein the predetermined amplitude value is a maximum amplitude value in the information regarding the first light source.

(4) The endoscopic apparatus according to the aspect (2) or (3) further comprising:

an observation mode selecting module that selects an observation mode from a plurality of observation modes having different emphasis objects in an observation image obtained by the image capturing module, wherein the light intensity ratio setting module sets the emitted light intensity ratio based on the selected observation mode.

(5) The endoscopic apparatus according to any one of aspects (2) to (4) further comprising:

a brightness information generating module that generates brightness information on the subject based on the captured signal output from the image capturing module, wherein the target light intensity setting module sets the target light intensity based on the brightness information.

(6) The endoscopic apparatus according to any one of aspects (1) to (5), wherein the first light source includes a light emitting diode and fluorescent substances, and the second light source includes a laser diode or a light emitting diode.

What is claimed is:

1. An endoscopic apparatus that outputs illuminating light from a tip of an endoscope inserting module to a subject and detects a reflected light from the subject to obtain an image signal of the subject, the endoscopic apparatus comprising:

a first light source that includes a first semiconductor light source having a relation between a light intensity of the first semiconductor light source and an amplitude value of a driving signal inputted to the first semiconductor light source, a part of the first relation being nonlinear;

a second light source that includes a second semiconductor light source emitting second light having different main wavelength component from the first light source;

a target light intensity setting module that sets a target light intensity for a sum of emitted light intensities from the first light source and the second light source;

a light intensity ratio setting module that sets an emitted light intensity ratio between the first light source and the second light source;

an information storing module that stores information representing relations between an amplitude value of imputed driving signal and the emitted light intensity for each of the first light source and the second light source;

an amplitude value setting module that sets a first amplitude value of the driving signal to be supplied to the first light source and a second amplitude value of the driving signal to be supplied to the second light source based on the emitted light intensity ratio set by the light intensity ratio setting module, the information stored in the information storing module, and the target light intensity set by the target light intensity setting module;

a driving signal generating module that generates a common driving signal common to the first light source and the second light source based on the target light intensity, generates a first driving signal for the first light source by changing the amplitude value of the common driving signal into the first amplitude value, and generates a second driving signal for the second light source by changing the amplitude value of the common driving signal into the second amplitude value; and a signal supplying module that controls the sum of the emitted light intensities to be the target light intensity by supplying the first driving signal to the first light source and supplying the second driving signal to the second light source, respectively.

2. The endoscopic apparatus according to claim 1 further comprising:

an image capturing module that captures the subject by adjusting an exposure period by an electronic shutter, wherein the driving signal generating module generates the common driving signal by performing, in the descending order of the target light intensity, when the target light intensity is in a range between a maximum intensity of the sum of the emitted light intensities and a threshold, a first pulse modulation control that reduces the number of driving pulses included in the driving signal until a predetermined lighting period for an exposure period in the one frame of the electronic shutter and a second pulse modulation control that reduces a density of the driving pulse by thinning-out the driving pulse, the driving signal generating module generates the driving signal where the density of the driving pulse is reduced to the limitation by the second pulse modulation control as the common driving signal when the target light intensity is lower than the threshold, the amplitude value setting module sets a predetermined amplitude value in the information as the first amplitude value and sets an amplitude value as the second amplitude value so that a ratio between the emitted light intensity from the first light source by the first amplitude value and the emitted light intensity from the second light source by the amplitude value becomes the light intensity ratio set by the light intensity setting module when the target light intensity is in the range from the maximum intensity to the threshold, and the amplitude value setting module sets the first amplitude value and the second amplitude value depending on the target light intensity when the target light intensity is lower than the threshold.

3. The endoscopic apparatus according to claim 2, wherein the predetermined amplitude value is a maximum amplitude value in the information regarding the first light source.

4. The endoscopic apparatus according to claim 2 further comprising:

an observation mode selecting module that selects an observation mode from a plurality of observation modes having different emphasis objects in an observation image obtained by the image capturing module, wherein the light intensity ratio setting module sets the emitted light intensity ratio based on the selected observation mode.

5. The endoscopic apparatus according to claim 3 further comprising:

an observation mode selecting module that selects an observation mode from a plurality of observation modes having different emphasis objects in an observation image obtained by the image capturing module, wherein the light intensity ratio setting module sets the emitted light intensity ratio based on the selected observation mode.

6. The endoscopic apparatus according to claim 2 further comprising:

a brightness information generating module that generates brightness information on the subject based on the captured signal output from the image capturing module, wherein the target light intensity setting module sets the target light intensity based on the brightness information.

7. The endoscopic apparatus according to claim 3 further comprising:

a brightness information generating module that generates brightness information on the subject based on the captured signal output from the image capturing module, wherein the target light intensity setting module sets the target light intensity based on the brightness information.

8. The endoscopic apparatus according to claim 4 further comprising:

a brightness information generating module that generates brightness information on the subject based on the captured signal output from the image capturing module, wherein the target light intensity setting module sets the target light intensity based on the brightness information.

9. The endoscopic apparatus according to claim 5 further comprising:

a brightness information generating module that generates brightness information on the subject based on the captured signal output from the image capturing module, wherein the target light intensity setting module sets the target light intensity based on the brightness information.

10. The endoscopic apparatus according to claim 1, wherein the first light source includes a light emitting diode and fluorescent substances, and the second light source includes a laser diode or a light emitting diode.

11. The endoscopic apparatus according to claim 2, wherein the first light source includes a light emitting diode and fluorescent substances, and the second light source includes a laser diode or a light emitting diode.

12. The endoscopic apparatus according to claim 3, wherein the first light source includes a light emitting diode and fluorescent substances, and the second light source includes a laser diode or a light emitting diode.

13. The endoscopic apparatus according to claim 4, wherein the first light source includes a light emitting diode and fluorescent substances, and the second light source includes a laser diode or a light emitting diode.

14. The endoscopic apparatus according to claim 5, wherein the first light source includes a light emitting diode and fluorescent substances, and the second light source includes a laser diode or a light emitting diode.

15. The endoscopic apparatus according to claim 6, wherein the first light source includes a light emitting diode and fluorescent substances, and the second light source includes a laser diode or a light emitting diode.

16. The endoscopic apparatus according to claim 7, wherein the first light source includes a light emitting diode and fluorescent substances, and the second light source includes a laser diode or a light emitting diode.

17. The endoscopic apparatus according to claim 8, wherein the first light source includes a light emitting diode and fluorescent substances, and the second light source includes a laser diode or a light emitting diode.

18. The endoscopic apparatus according to claim 9, wherein the first light source includes a light emitting diode and fluorescent substances, and the second light source includes a laser diode or a light emitting diode.

\* \* \* \* \*